United States Patent [19]
Saikusa et al.

[11] Patent Number: 5,472,730
[45] Date of Patent: Dec. 5, 1995

[54] γ-AMINOBUTYRIC ACID-ENRICHED FOOD MATERIAL AND METHOD FOR PRODUCING γ-AMINOBUTYRIC ACID

[75] Inventors: Takayo Saikusa, Fukuyama; Yutaka Mori, Tsukuba; Toshiroh Horino, Fukuyama, all of Japan

[73] Assignee: Director General of Chugoku National Agricultural Experiment Station, Ministry of Agriculture, Forestry and Fisheries, Fukuyama, Japan

[21] Appl. No.: 297,597

[22] Filed: Aug. 29, 1994

[30] Foreign Application Priority Data

Feb. 1, 1994 [JP] Japan .................................... 6-027581

[51] Int. Cl.$^6$ .............................. A23J 1/12; A23L 1/305; A23L 1/172
[52] U.S. Cl. .......................... 426/618; 426/655; 426/656; 562/433
[58] Field of Search .................................... 426/618, 656, 426/655

[56] References Cited

U.S. PATENT DOCUMENTS 4,786,647  11/1988  Simpkins et al. .
5,215,750   6/1993  Keane, II .

*Primary Examiner*—Donald E. Czaja
*Assistant Examiner*—Choon Park Koh
*Attorney, Agent, or Firm*—Frishauf, Holtz, Goodman, Langer & Chick

[57] ABSTRACT

Disclosed are γ-aminobutyric acid-enriched food materials to be obtained by dipping at least one material chosen from among germs of rice, rice bran containing germs, whole rice, germs of wheat and wheat bran containing germs in water at a pH of from 2.5 to 7.5 and at 80° C. or lower. Also disclosed is a method for producing γ-aminobutyric acid by extracting the γ-aminobutyric acid-enriched food material with an acid followed by purifying the resulting extract by ion-exchanging chromatography. These products are useful as particular nutrient foods or additives to foods for patients suffering from hypertension.

15 Claims, 6 Drawing Sheets

γ-AMINOBUTYRIC ACID-ENRICHED FOOD MATERIAL AND METHOD FOR PRODUCING γ-AMINOBUTYRIC ACID

FIELD OF THE INVENTION

The present invention relates to a γ-aminobutyric acid-enriched food material and a method for producing γ-aminobutyric acid. More precisely, it relates to a γ-aminobutyric acid-enriched food material to be prepared by dipping at least one material chosen from among germs of rice, rice bran containing germs, whole rice, germs of wheat and wheat bran containing germs in water under pre-determined conditions so as to greatly increase the content of γ-aminobutyric acid in the material due to the activity of the endogenous enzyme therein. It also relates to a method for producing γ-aminobutyric acid by extracting the γ-aminobutyric acid-enriched food material with an acid followed by purifying and concentrating the resulting extract by ion-exchanging chromatography.

BACKGROUND OF THE INVENTION

γ-Aminobutyric acid is a kind of amino acid that is produced by decarboxylation of glutamic acid in living organisms, and it is known that the acid plays an important role in the central nervous system as a neurotransmitter and, in addition, has a function to lower the blood pressure in animals including human beings.

Recently, it has been found that the content of γ-aminobutyric acid in tea leaves may be increased to 5 to 10 times by anaerobically treating raw tea leaves. At present, such tea having an increased content of γ-aminobutyric acid has been commercially sold by various makers as "Gabaron Tea" (trade name). "Gabaron Tea" has been proved to have an effect of curing hypertension by animal tests and has been utilized by persons suffering from hypertension as an easy means to cure hypertension without minding its side effect.

It is said necessary to perorally take a large amount of γ-aminobutyric acid so as to lower the blood pressure in hypertension. For "Gabaron Tea", however, it is difficult to take a large amount of γ-aminobutyric acid therefrom since the tea is diluted when extracted with hot water. This will be the reason why "Gabaron Tea" is considered ineffective against hypertension by some persons.

At present, γ-aminobutyric acid is produced by fermentation, which, however, is not satisfactory in view of its cost. Under these situations, desired are the development of food materials from which a higher concentration of γ-aminobutyric acid may be taken and the development of a method for producing a safe and low-priced γ-aminobutyric acid.

SUMMARY OF THE INVENTION

We, the present inventors have found that a high concentration of glutamic acid which is a precursor of γ-aminobutyric acid is contained in the surface layer parts of germs, rice grains and wheat grains and that the glutamic acid is rapidly converted into γ-aminobutyric acid while dipped in water. On the basis of these findings, we have completed the present invention.

Specifically, the present invention provides a γ-aminobutyric acid-enriched food material to be obtained by dipping at least one material chosen from among germs of rice, rice bran containing germs, whole rice, germs of wheat and wheat bran containing germs in water at a pH of from 2.5 to 7.5 and at 80° C. or lower. It also provides a method for producing γ-aminobutyric acid by extracting the γ-aminobutyric acid-enriched food material with an acid followed by purifying the resulting extract by ion-exchanging chromatography.

DETAILED DESCRIPTION OF THE INVENTION

Figure 1:
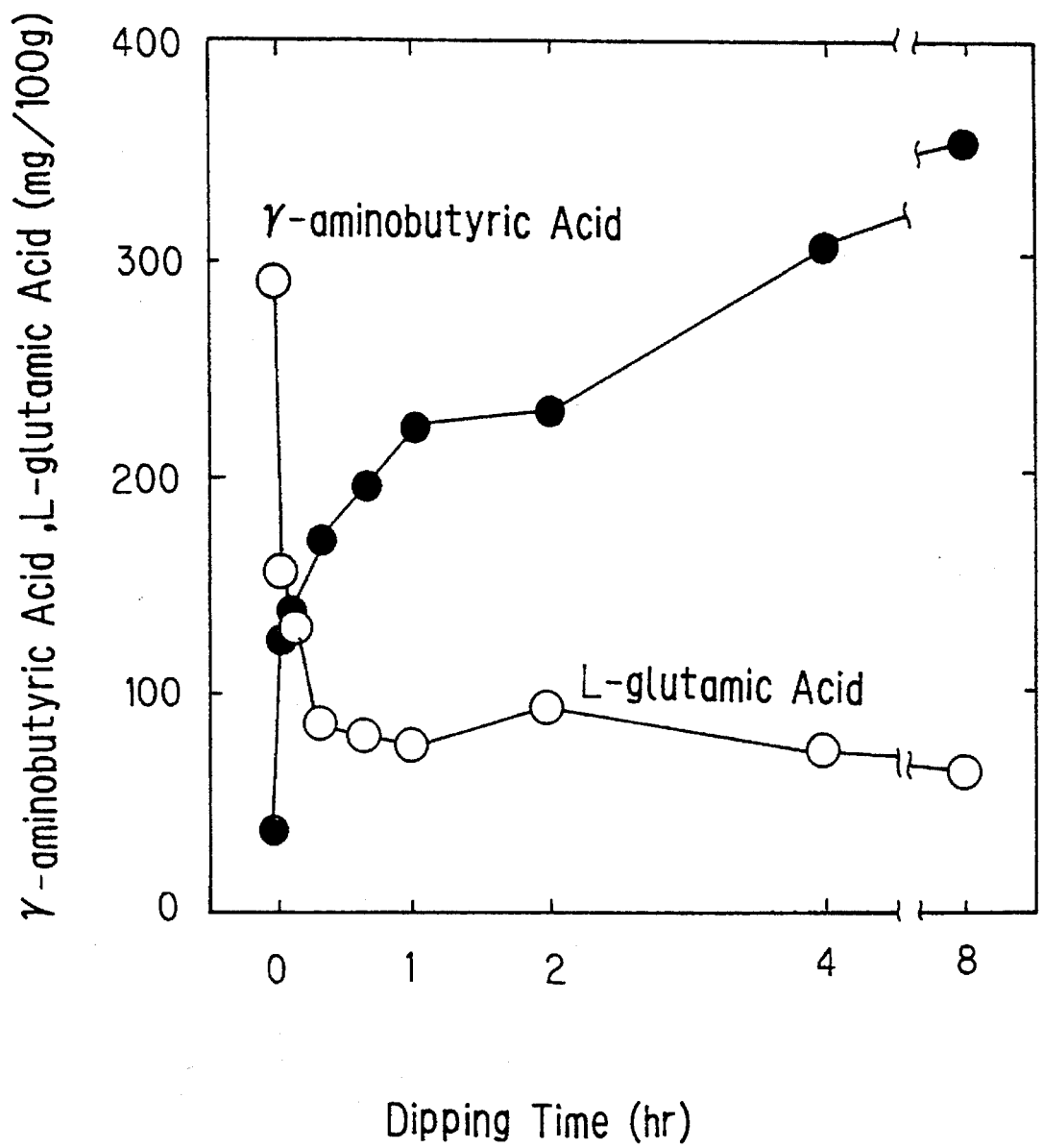
FIG. 1 is a graph showing the relationship between γ-aminobutyric acid accumulated and the decrement in the glutamic acid content in the process of Example 1.

Varieties of rice and wheat to be used in the present invention are not specifically defined, but preferred are those having a high proportion by weight of germs such as giant germ rice as well as those capable of producing a large amount of γ-aminobutyric acid (e.g., rice of Hokkai No. 269, and wheat of Shirasagi-komugi).

Whole rice may be easily prepared by cleaning rice in an ordinary rice-cleaning mill (for example, RMA-150 Model, made by Yanagisawa Seisaku-sho KK) to remove rice bran therefrom. Germs may be separated from whole rice by polishing it in a rice-polishing mill (for example, TM5 Model, made by Satake Seisaku-sho KK) followed by sieving the resulting albumen-derived rice powder and bran through a suitable sieve (of around 32-mesh) to separate germs therefrom.

On the other hand, germs of wheat and wheat bran containing germs may be obtained by milling wheat in a wheat mill (for example, Pullar Type Test Mill, made by Pullar Co.) to separate wheat bran (fine wheat bran, coarse wheat bran) therefrom. The thus-separated wheat bran (especially, fine wheat bran) is then sieved through a sieve of around 50-mesh or a finer sieve than that to be employed for obtaining germs of rice to further separate germs of wheat therefrom. As the wheat bran, preferred is fine wheat bran.

To prepare a γ-aminobutyric acid-enriched food material, water having a pH of from 2.5 to 7.5, preferably from 3.0 to 7.0, more preferably from 5.5 to 6.0 is added to at least one material chosen from among the above-mentioned germs of rice, rice bran containing germs, whole rice, germs of wheat and wheat bran containing germs, in an amount of from 2 to 10 times as large as the amount of the material, and shaken at 80° C. or lower, generally at a temperature of from 10° to 70° C. and at a shaking speed of from 50 to 150 strokes/min for a period of 20 minutes or more, generally from 20 minutes to 48 hours, preferably at a shaking speed of from 80 to 120 strokes/min for a period of from 1 to 48 hours, more preferably at 40° C. and at a shaking speed of 100 strokes/min for a period of from 4 to 48 hours. Acids may be used for adjusting the pH value of the water to be used, which may be either organic acids or inorganic acids.

Preferred are organic acids such as acetic acid, citric acid and malic acid, and inorganic acids such as hydrochloric acid, sulfuric acid and phosphoric acid. Alkalis may also be used for the same purpose, which include, for example, sodium hydroxide, potassium hydroxide, calcium hydroxide, sodium carbonate and sodium phosphate.

By the treatment, the glutamate decarboxylase existing in germs acts on the glutamic acid therein to convert the acid into γ-aminobutyric acid. During the treatment, the protease in germs, etc. also acts on proteins therein to decompose them into glutamic acid. Accordingly, the conversion of glutamic acid into γ-aminobutyric acid is effected efficiently by the treatment.

Where Koshihikari rice, which is the most popular variety of rice to be boiled to eat, is subjected to the above-mentioned treatment, the γ-aminobutyric acid content in its germs may be increased to about 400 mg/100 g. Considering the fact that the γ-aminobutyric acid content in "Gabaron Tea" is about 170 mg per 100 g of the dry leaves, γ-aminobutyric acid can be accumulated in the germs of Koshihikari rice in an amount of 2 times or more than that in "Gabaron Tea" by the treatment.

Where γ-aminobutyric acid is taken from "Gabaron Tea" or germs, "Gabaron Tea" shall be extracted and diluted with hot water and the thus-diluted extract is drunk while germs may directly be eaten as they are in whole rice or in food materials without being diluted. Accordingly, germs may be utilized as more effective γ-aminobutyric acid sources.

To produce γ-aminobutyric acid, an acid is added to at least one food material of germs of rice, rice bran containing germs, whole rice, germs of wheat and wheat bran containing germs that have been treated by the above-mentioned dipping treatment to thereby extract the acid from the material. Concretely, an acid chosen from among inorganic acids such as hydrochloric acid, sulfuric acid and phosphoric acid and organic acids such as acetic acid, citric acid and malic acid is added to the material, by which the material is made acidic, preferably strongly acidic to have a pH of from 1 to 2, and thereafter the material is shaken at a temperature of from 0° to 70° C., preferably from 10° to 40° C., and at a shaking speed of from 50 to 150 strokes/min for 5 minutes to 2 hours, preferably at a shaking speed of 100 strokes/min for one hour, to thereby extract γ-aminobutyric acid from the material. Next, the resulting extract is subjected to solid-liquid separation, for example, by centrifugation (3000 rpm, 10 minutes) or filtration to recover the supernatant (liquid extract).

Next, the liquid extract is purified and concentrated by ion-exchanging chromatography. The ion-exchanging chromatography may be conducted, for example, under the conditions shown in Table 1 below, thereby giving a pure γ-aminobutyric acid. The thus-obtained γ-aminobutyric acid is sweet and tasty and may be utilized as a food additive or seasoning. The amount of the acid to be used for this purpose may be determined according to the intended object.

TABLE 1

Conditions for Purifying γ-Aminobutyric Acid

1. System
    L-8500 Model high-performance amino acid analyzer
    (made by Hitachi Ltd.)
2. Separation Column
    Column filled with Lithium Ion-exchanging Gel 2622
    (made by Mitsubishi Kasei Corp.)
3. Eluents TABLE 1-continued Conditions for Purifying γ-Aminobutyric Acid

| | | |
|---|---|---|
| 1) | Lithium citrate 4-hydrate | 5.73 g |
| | Lithium chloride | 1.24 g |
| | Citric acid | 19.90 g |
| | Ethyl alcohol | 30.0 ml |
| | Thiodiglycol | 5.0 ml |
| | BRIJ-35 | 1.00 g |
| | Distilled water to make | 1.0 liter |
| 2) | Lithium citrate 4-hydrate | 9.80 g |
| | Lithium chloride | 6.36 g |
| | Citric acid | 12.00 g |
| | Ethyl alcohol | 30.00 ml |
| | Thiodiglycol | 5.0 ml |
| | BRIJ-35 | 1.00 g |
| | Distilled water to make | 1.0 liter |
| 3) | Lithium citrate 4-hydrate | 8.79 g |
| | Lithium chloride | 26.62 g |
| | Citric acid | 11.27 g |
| | Ethyl alcohol | 100.0 ml |
| | Benzyl alcohol | 3.0 ml |
| | BRIJ-35 | 1.00 g |
| | Distilled water to make | 1.0 liter |
| 4) | Lithium citrate 4-hydrate | 9.80 g |
| | Lithium chloride | 28.15 g |
| | Citric acid | 3.30 g |
| | BRIJ-35 | 1.00 g |
| | Distilled water to make | 1.0 liter |

4. Conditions for Elution

| Time for Elution (min) | Eluent (%) | | | | Column Temperature (°C.) |
|---|---|---|---|---|---|
| | 1 | 2 | 3 | 4 | |
| 0 to 10 | 100 | 0 | 0 | 0 | 30 |
| 10 to 18 | 100 | 0 | 0 | 0 | 32 |
| 18 to 21 | 80 | 20 | 0 | 0 | 32 |
| 21 to 32 | 80 | 20 | 0 | 0 | 52 |
| 32 to 39 | 10 | 90 | 0 | 0 | 52 |
| 39 to 43 | 10 | 90 | 0 | 0 | 45 |
| 43 to 49 | 0 | 100 | 0 | 0 | 45 |
| 49 to 67 | 0 | 0 | 100 | 0 | 70 |
| 67 to 76 | 0 | 0 | 100 | 0 | 45 |
| 76 to 92 | 0 | 0 | 0 | 100 | 45 |
| 92 to 107 | 0 | 0 | 0 | 100 | 70 |

According to the present invention that has been described in detail hereinabove, food materials containing a high concentration of γ-aminobutyric acid and a high-purity γ-aminobutyric acid are obtained from at least one material chosen from among germs of rice, rice bran containing germs, whole rice, germs of wheat and wheat bran containing germs, which have heretofore been utilized only as sources for edible oil, by simple operation. Such γ-aminobutyric acid-enriched food materials and high-purity γ-aminobutyric acid may be utilized as particular nutrient foods or additives to foods for patients suffering from hypertension.

While the invention has been described in detail and with reference to specific embodiments thereof, it will be apparent to one skilled in the art that various changes and modifications can be made therein without departing from the spirit and scope thereof.

The present invention will be explained in more detail by means of the following examples, which, however, are not intended to restrict the scope of the present invention.

EXAMPLE 1

4 ml of distilled water were added to 0.2 g of germs derived from Koshihikari rice and shaken at 40° C. and at a shaking speed of 100 strokes/min, by which γ-aminobutyric acid precipitated. Precisely, as shown in FIG. 1, γ-aminobutyric acid was accumulated rapidly with decrease of glutamic acid and reached 360 mg/100 g after 8 hours. Considering the fact that the γ-aminobutyric acid content in non-treated germs is about 25 mg/100 g, it is noted that the γ-aminobutyric acid content in the thus-treated germs increased to 14.4 times. After 20 minutes from the start of the treatment, the decrement in the glutamic acid content became small relative to the amount of the γ-aminobutyric acid formed. From this, it is presumed that glutamic acid was supplemented by decomposition of proteins, etc. during the treatment.

EXAMPLE 2

Figure 2:
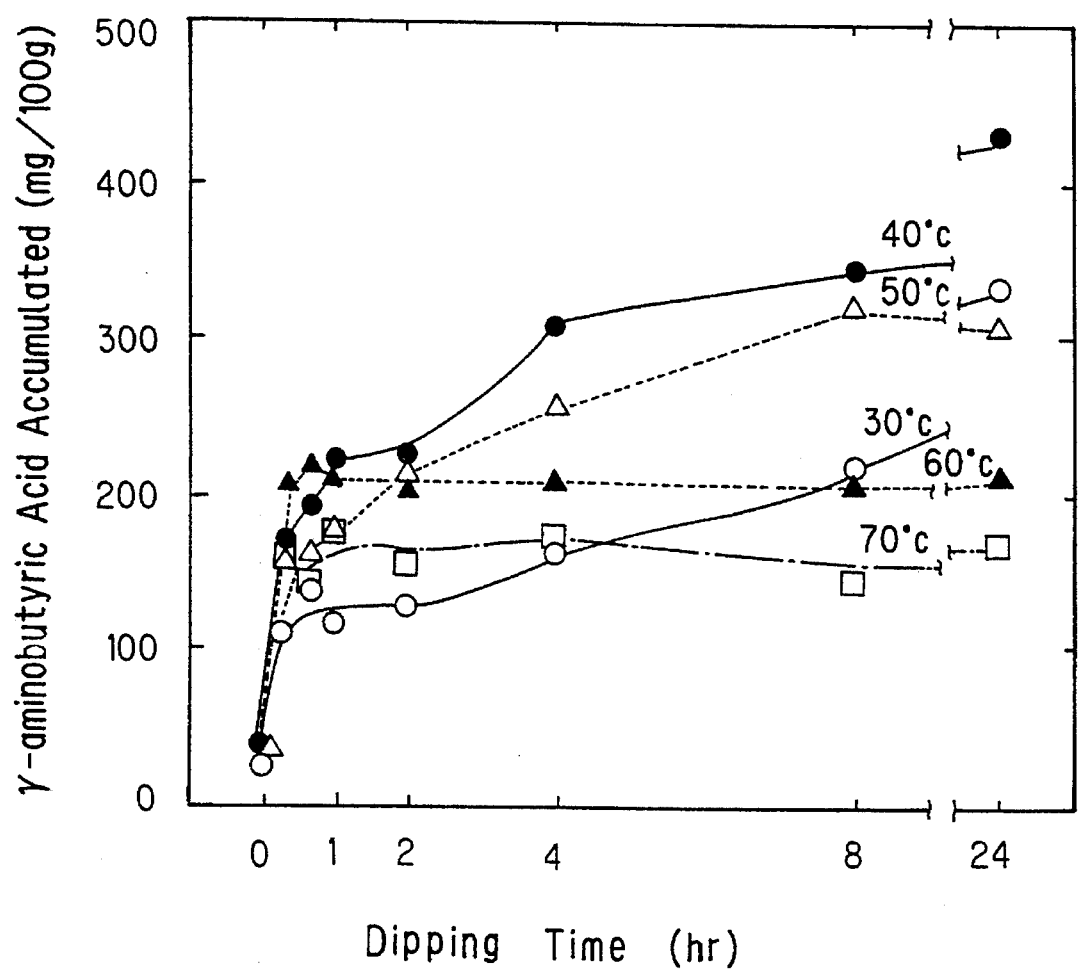
FIG. 2 is a graph showing γ-aminobutyric acid accumulated in the process of Example 2.

Germs of Koshihikari rice were treated at a temperature of from 30° to 70° C. in the same manner as in Example 1 to produce γ-aminobutyric acid. The results are shown in FIG. 2, from which it is noted that 40° C. is the optimum treating temperature at which the amount of γ-aminobutyric acid produced was the highest and the producing speed was also the highest.

EXAMPLE 3

Figure 3:
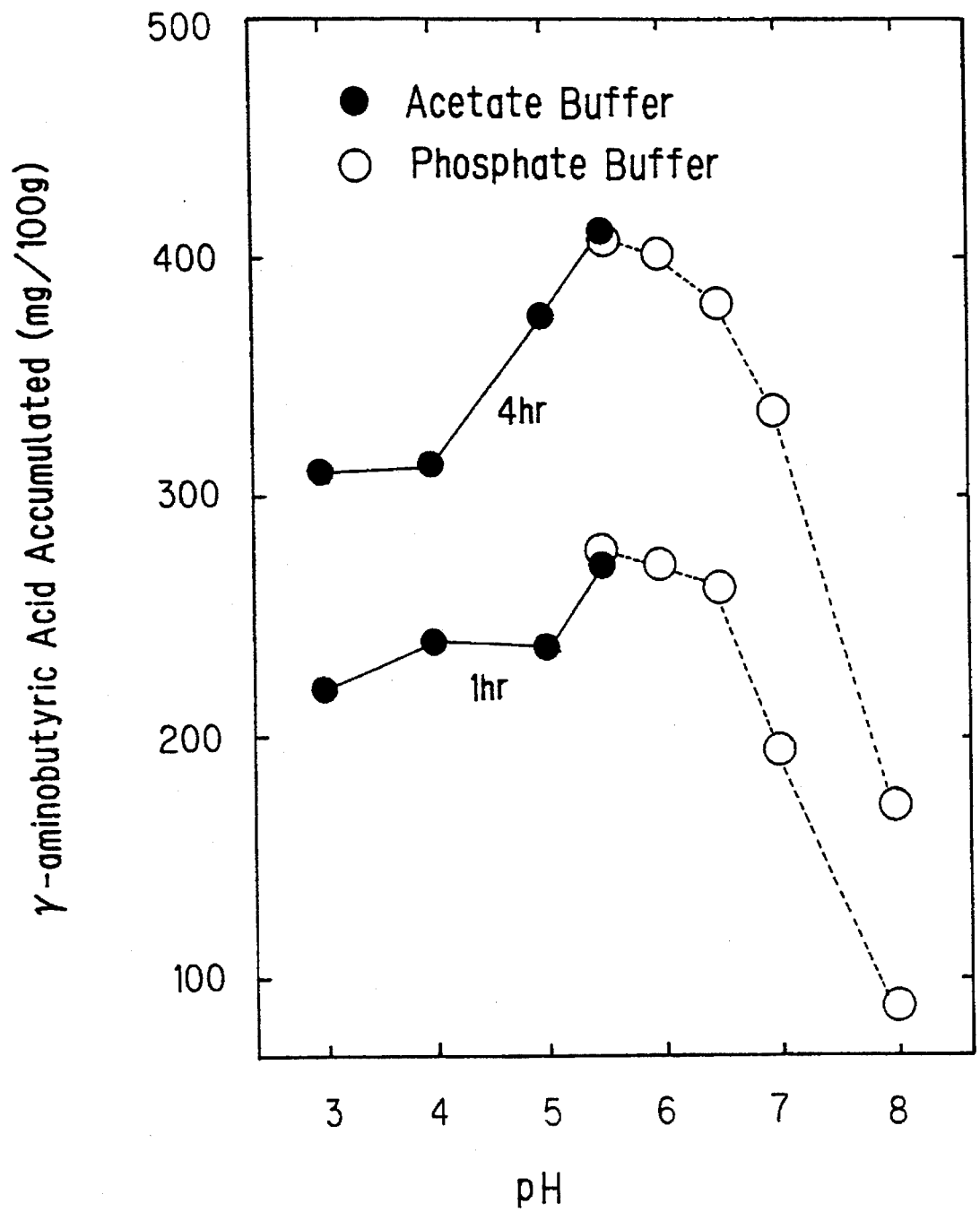
FIG. 3 is a graph showing γ-aminobutyric acid accumulated in the process of Example 3.

Germs of Koshihikari rice were treated at a pH of from 3 to 8 in the same manner as in Example 1 to produce γ-aminobutyric acid. The results are shown in FIG. 3, from which it is noted that the optimum pH range in producing γ-aminobutyric acid by the treatment is from 5.5 to 6.0 whilst the amount of γ-aminobutyric acid produced suddenly decreased under the alkaline condition.

EXAMPLE 4

Figure 4:
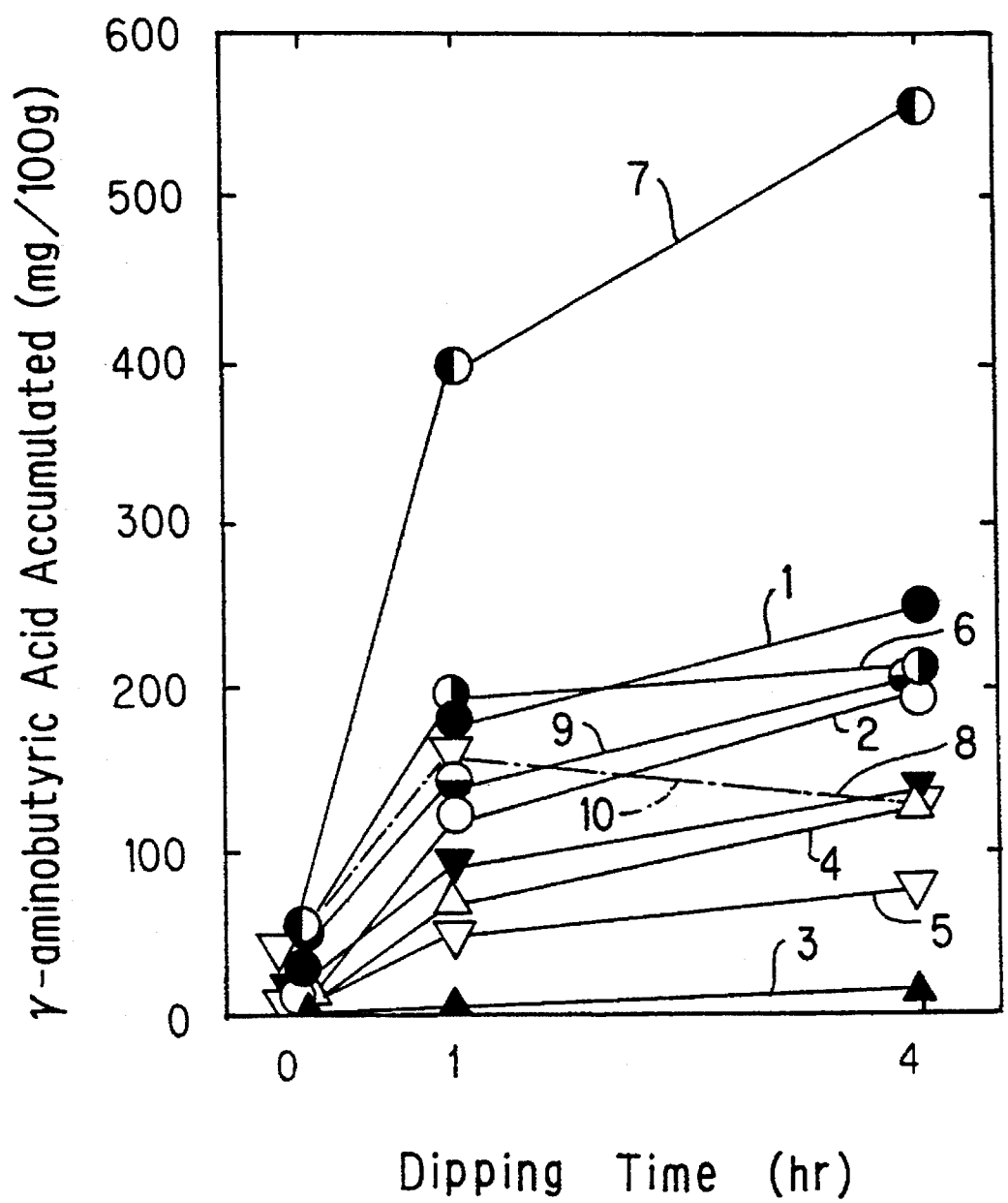
FIG. 4 is a graph showing γ-aminobutyric acid accumulated in the process of Example 4.

Germs derived from different 10 varieties of rice shown in Table 2 below were treated under the same conditions as those in Example 1 to produce γ-aminobutyric acid. Table 2 shows the characteristics of rice used and the weight of germs in rice. The results are shown in FIG. 4, from which it is noted that the amount of γ-aminobutyric acid formed greatly varied, depending on the variety of rice used. Briefly, Takanari rice did not almost produce the acid, while Hokkai No. 269 rice produced the acid in an amount of 2 times as large as that produced by Koshihikari rice.

TABLE 2

| Amount (by weight) of Germs in Rice | | |
|---|---|---|
| Variety of Rice | Characteristics | Amount of Germs (wt. %) |
| 1. Koshihikari | Eating-quality rice | 3.5 |
| 2. Aya | Low-amylose rice | 3.5 |
| 3. Takanari | High-yield rice | 3.0 |
| 4. Ohchikara | Giant-grain rice | 3.6 |
| 5. Kitakaori | Sweet-smelling rice | 2.7 |
| 6. Chugoku No. 137 | Giant-germ rice | 10.3 |
| 7. Hokkai No. 269 | Giant-germ rice | 9.0 |
| 8. Chugoku-mochi No. 120 | For rice cake | 2.4 |
| 9. Himenomochi | For rice cake | 3.0 |
| 10. Hoshiyutaka | Long-grain | 4.3 |

It has been found that Hokkai No. 269 rice gave γ-aminobutyric acid of 560 mg/100 g, after treated for 4 hours. The amount of the acid produced by Hok kai No. 269 rice is about 3 times as large as that produced by "Gabaron Tea". Hokkai No. 269 rice is giant-germ rice, having germs of nearly 3 times as large as those in ordinary rice, and it is the best as the raw material for producing γ-aminobutyric acid.

EXAMPLE 5

Figure 5:
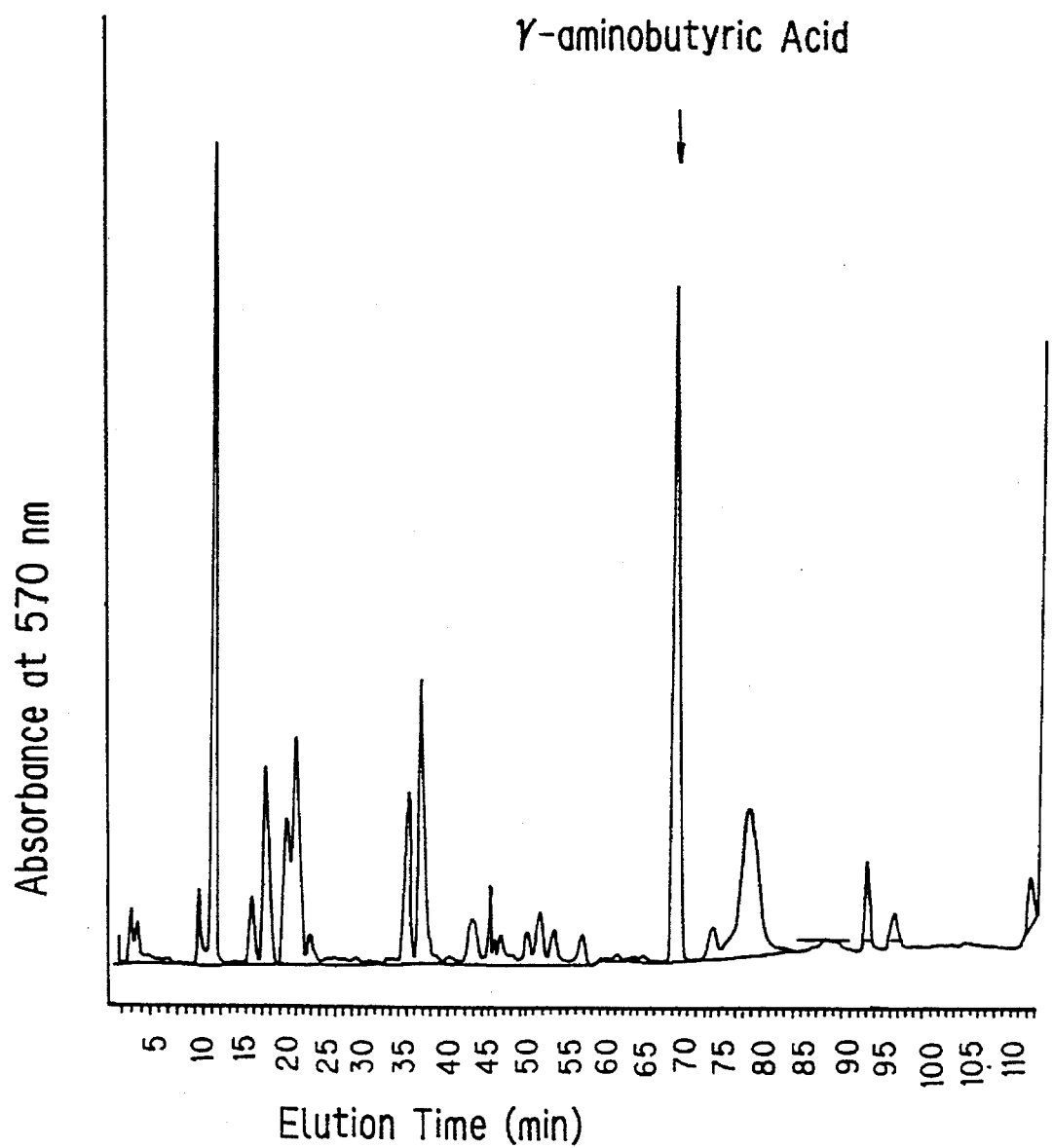
FIG. 5 is a separation chart of γ-aminobutyric acid by ion-exchanging chromatography in the process of Example 5.

Germs of Hokkai No. 269 rice were treated for 4 hours under the same conditions as those in Example 1 to produce a liquid containing γ-aminobutyric ac. 1N hydrochloric acid was added to the liquid in an amount of ⅕ of the liquid and shaken at a shaking speed of 100 strokes/min to extract γ-aminobutyric acid therefrom at 30° C. for a time more than 5 minutes. Next, the resulting extrct was centrifuged for 10 minutes at 3000 rpm to remove the insoluble substances therefrom and then subjected to ion-exchanging chromatography under the same conditions as those shown in Table 1 above to separate γ-aminobutyric acid therefrom. The results are shown in FIG. 5. Next, the thus-separated γ-aminobutyric acid was collected, using a fraction collector. By the operation, obtained were 5.2 mg of γ-aminobutyric acid from one g of germs of Hokkai No. 269 rice.

EXAMPLE 6

Figure 6:
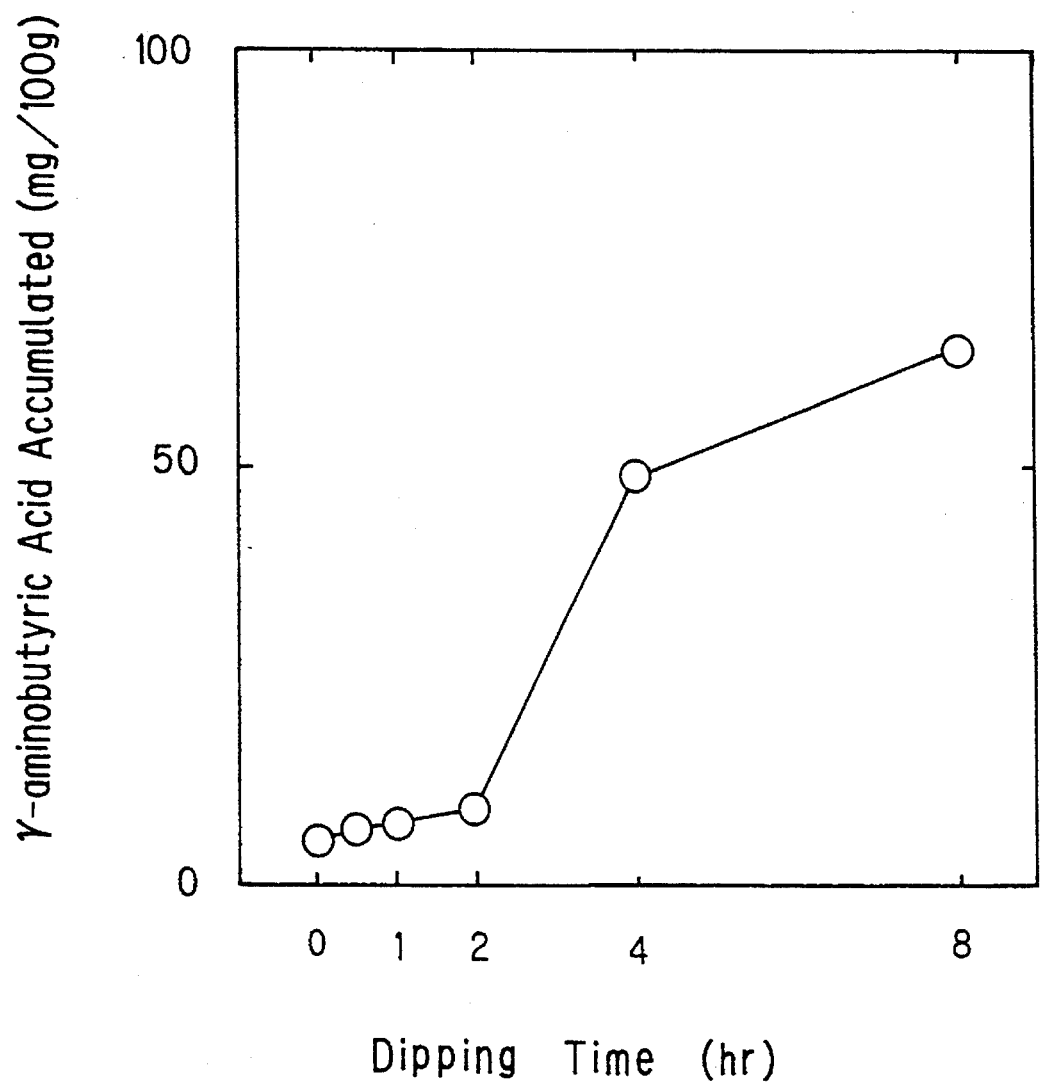
FIG. 6 is a graph showing γ-aminobutyric acid accumulated in the process of Example 6.

8 ml of 1M phosphate buffer (pH 5.5) were added to 0.5 g of fine wheat bran derived from Shirasagi-komugi (a variety of wheat) and shaken at 40° C. at a shaking speed of 100 strokes/min, by which precipitated γ-aminobutyric acid, as shown in FIG. 6. Precisely, γ-aminobutyric acid began to precipitate after shaking the germs for 2 hours or more along with the buffer and reached 63.7 mg/100 g after 8 hours.

What is claimed is:

1. A γ-aminobutyric acid-enriched material obtained by dipping at least one material chosen from among germs of rice, rice bran containing germs, whole rice, germs of wheat and wheat bran containing germs in water at a pH of from 2.5 to 7.5 and at 80° C. or lower.

2. A method for producing γ-aminobutyric acid comprising extracting a γ-aminobutyric acid-enriched material, which is obtained by dipping at least one material selected from the group consisting of germs of rice, rice bran containing germs, whole rice, germs of wheat and wheat bran containing germs in water at a pH of from 2.5 to 7.5 and at 80° C. or lower, with an acid followed by purifying the resulting extract by ion-exchanging chromatography.

3. The γ-aminobutyric acid-enriched material of claim 1 wherein said at least one material is dipped into water which has a pH of from 3 to 7 at a temperature of from 10° to 70° C. and agitated for at least 20 minutes and said water is in an amount at least 2 times the amount of said at least one material.

4. The γ-aminobutyric acid-enriched material of claim 3 wherein said at least one material is dipped into water which has a pH of from 5.5 to 6 and agitated for from 20 minutes to 48 hours and said water is in an amount of from 2 to 10 times the amount of said at least one material.

5. The γ-aminobutyric acid-enriched material of claim 4 wherein said at least one material is dipped into water and agitated at a temperature of about 40° C. for from 1 to 48 hours.

6. The γ-aminobutyric acid-enriched material of claim 1 wherein said at least one material is dipped into water to which acid has been added to adjust the pH to from 1 to 2 at a temperature of from 0° to 70° C. for at least 5 minutes with agitation, said water being in an amount of at least twice the amount of said at least one material.

7. The γ-aminobutyric acid-enriched material of claim 6 wherein said water is at a temperature of from 10° to 40° C. and agitation is carried out for about 1 hour.

8. The γ-aminobutyric acid-enriched material of claim 6 wherein said acid is selected from the group consisting of acetic acid, citric acid, malic acid, hydrochloric acid, sulfuric acid and phosphoric acid.

9. A method for producing γ-aminobutyric acid-enriched material comprising dipping at least one material selected from the group consisting of germs of rice, rice bran containing germs, whole rice, germs of wheat and wheat bran containing germs in water which is at a pH of from 2.5 to 7.5 and at a temperature not more than 80° C. with agitation of said at least one material in said water.

10. A method for producing γ-aminobutyric acid-enriched material of claim 9 wherein said at least one material is dipped into water which has a pH of from 3 to 7 at a temperature of from 10° to 70° C. and agitated for at least 20 minutes and said water is in an amount at least 2 times the amount of said at least one material.

11. A method for producing γ-aminobutyric acid-enriched material of claim 10 wherein said at least one material is dipped into water which has a pH of from 5.5 to 6 and agitated for from 20 minutes to 48 hours and said water is in an amount of from 2 to 10 times the amount of said at least one material.

12. A method for producing γ-aminobutyric acid-enriched material of claim 11 wherein said at least one material is dipped into water and agitated at a temperature of about 40° C. for from 1 to 48 hours.

13. A method for producing γ-aminobutyric acid-enriched material of claim 9 wherein said at least one material is dipped into water to which acid has been added to adjust the pH to from 1 to 2 at a temperature of from 0° to 70° C. for at least 5 minutes with agitation, said water being in an amount of at least twice the amount of said at least one material.

14. A method for producing γ-aminobutyric acid-enriched material of claim 13 wherein said water is at a temperature of from 10° to 40° C. and agitation is carried out for about 1 hour.

15. A method for producing γ-aminobutyric acid-enriched material of claim 13 wherein said acid is selected from the group consisting of acetic acid, citric acid, malic acid, hydrochloric acid, sulfuric acid and phosphoric acid.

* * * * *